(12) United States Patent
Miyazawa

(10) Patent No.: US 8,257,776 B2
(45) Date of Patent: Sep. 4, 2012

(54) SURFACE MODIFICATION METHOD AND SURFACE MODIFIED MATERIAL

(75) Inventor: Kazuyuki Miyazawa, Yokohama (JP)

(73) Assignee: Shiseido Company, Ltd, Tokyo (JP)

( * ) Notice: Subject to any disclaimer, the term of this patent is extended or adjusted under 35 U.S.C. 154(b) by 254 days.

(21) Appl. No.: 12/738,878

(22) PCT Filed: Oct. 15, 2008

(86) PCT No.: PCT/JP2008/068675
§ 371 (c)(1),
(2), (4) Date: Apr. 20, 2010

(87) PCT Pub. No.: WO2009/054299
PCT Pub. Date: Apr. 30, 2009

(65) Prior Publication Data
US 2010/0221558 A1    Sep. 2, 2010

(30) Foreign Application Priority Data
Oct. 25, 2007    (JP) ................... 2007-277361

(51) Int. Cl.
A61L 33/00    (2006.01)
C07F 7/00    (2006.01)

(52) U.S. Cl. .......................... 427/2.1; 556/400

(58) Field of Classification Search ............ None
See application file for complete search history.

(56) References Cited

U.S. PATENT DOCUMENTS

| 4,395,463 A | 7/1983 | Kray |
| 6,326,011 B1 * | 12/2001 | Miyazawa et al. ............ 424/401 |
| 6,846,567 B1 | 1/2005 | Ekinaka et al. |
| 2005/0042462 A1 * | 2/2005 | Fehn et al. .................... 428/447 |
| 2006/0020098 A1 * | 1/2006 | Miyazawa et al. ............... 528/28 |
| 2006/0060533 A1 * | 3/2006 | Miyazawa et al. ............ 210/656 |
| 2008/0214855 A1 * | 9/2008 | Toujo et al. .................... 556/405 |

FOREIGN PATENT DOCUMENTS

| JP | 7-118123 | 5/1995 |
| JP | 8-277379 | 10/1996 |
| JP | 11-302129 | 11/1999 |
| JP | 2000-279512 | 10/2000 |
| JP | 2002-098676 | 4/2002 |
| JP | 2006-187456 | 7/2005 |
| JP | 2006-011380 | 1/2006 |
| JP | 2006-011381 | 1/2006 |
| JP | 2006-011383 | 1/2006 |
| JP | 2006-239636 | 9/2006 |
| JP | 2006-274260 | 10/2006 |
| JP | 2007-119643 | 5/2007 |
| WO | WO 2005054262 A1 * | 6/2005 |
| WO | WO 2006/083339 | 8/2006 |

OTHER PUBLICATIONS

Extended European Search Report mailed Oct. 29, 2010.

* cited by examiner

*Primary Examiner* — Michael Cleveland
*Assistant Examiner* — Francisco Tschen
(74) *Attorney, Agent, or Firm* — IPUSA, PLLC

(57) ABSTRACT

A surface modification method includes a step of applying, onto a material, an application fluid containing a polymer having a functional group capable of producing a silanol group through hydrolysis thereof and an alkoxysilane and a step of applying, onto the material on which the application fluid is applied, an application fluid containing a hydrophilizing agent having a functional group capable of producing a silanol group through hydrolysis thereof or a silanol group.

5 Claims, 1 Drawing Sheet

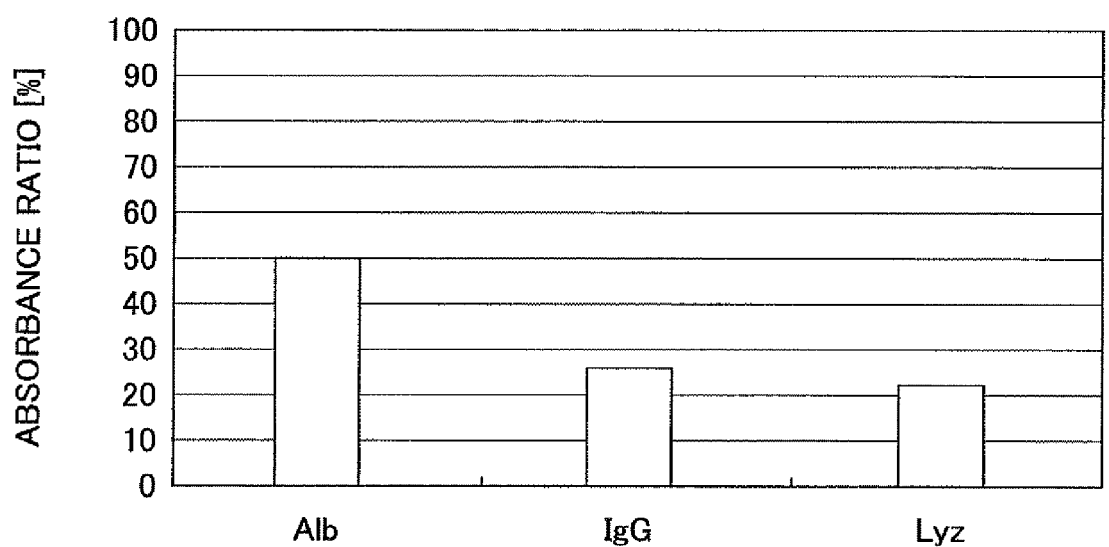

ent invention relates to a surface modification
SURFACE MODIFICATION METHOD AND SURFACE MODIFIED MATERIAL

TECHNICAL FIELD

The present invention relates to a surface modification method and a surface modified material.

BACKGROUND ART

Conventionally, a polymer having a phosphorylcholine group is known as a biocompatible polymer and a biocompatible material is known in which each kind of a resin material is coated with such a polymer.

Japanese Patent Application Publication No. 07-118123 discloses that a powder body is coated with a polymer obtained by polymerizing 2-methacryloyloxyethylphosphorylcholine as one monomer whereby it is possible to obtain a powder body for cosmetic material which is not readily removable, is excellent in the proceeding of a modification effect thereof, and is excellent in the moisture retention thereof.

Furthermore, Japanese Patent Application Publication No. 2000-279512 discloses a medical material in which a coating layer composed of a copolymer of a monomer having a phosphorylcholine-like group as a side chain thereof and a monomer having a group capable of bonding to heparin or a heparin derivative, and heparin or a heparin derivative is formed on the surface of a substrate. Such a medical material allows for excellent antithrombogenicity and biocompatibility over a long period of time which are suitable for various kinds of medical materials such as catheters, guide wires, artificial vessels, haemodialysis membranes, and endoscopes.

Moreover, Japanese Patent Application Publication No. 2002-098676 discloses a separation material having a phosphorylcholine-like group on at least the surface thereof, wherein the ratio (P/C) of the quantity of phosphorus element P originating from the phosphorylcholine-like group to the quantity of carbon element C is 0.002-0.3 for the spectrum measured by means of an X-ray photoelectron spectroscopic analysis of the surface. It is possible for such a separation material to electively separate a wide variety of specific components, in particular, cells, proteins or signaling substances originating from an organism, etc., and further recover those components.

Meanwhile, Japanese Patent Application Publication No. 2006-011381 discloses a method in which an ophthalmic lens material is subjected to plasma treatment to introduce a hydroxyl group therein and subsequently reacted with a compound having a phosphorylcholine group and a carboxyl group in an organic solvent to cause covalent bonding via an ester bond. Furthermore, Japanese Patent Application Publication No. 2006-011383 discloses a method in which an OH group is introduced in the surface of an ophthalmic lens material by means of plasma treatment and subsequently reaction with a compound having a phosphorylcholine group and an aldehyde group is conducted in water, an organic solvent or a water-organic solvent mixed liquid to cause covalent bonding via an acetal bond. However, it is difficult to introduce a phosphorylcholine-like group in a surface of a resin material such as PEEK (polyetheretherketone) or a fluororesin by means of plasma treatment.

DISCLOSURE OF THE INVENTION

According to one aspect of the present invention, there is provided a surface modification method including a step of applying, onto a material, an application fluid containing a polymer having a functional group capable of producing a silanol group through hydrolysis thereof and an alkoxysilane and a step of applying, onto the material on which the application fluid is applied, an application fluid containing a hydrophilizing agent having a functional group capable of producing a silanol group through hydrolysis thereof or a silanol group.

According to another aspect of the present invention, there is provided a surface modified material, wherein a surface thereof is modified by using a surface modification method as described above.

BRIEF DESCRIPTION OF THE DRAWINGS

FIG. 1 is a diagram illustrating an evaluation result of the amounts of adsorbed proteins in a practical example.

BEST MODE FOR CARRYING OUT THE INVENTION

Next, the best mode for carrying out the present invention will be described in conjunction with the drawing.

A surface modification method according to the present invention includes a step of applying, onto a material, an application fluid containing a polymer having a functional group capable of producing a silanol group through hydrolysis thereof (referred to as a "hydrolyzable polymer" below) and an alkoxysilane and a step of applying, onto the material on which the application fluid is applied, an application fluid containing a hydrophilizing agent having a functional group capable of producing a silanol group through hydrolysis thereof or a silanol group. Thereby, it is possible to hydrophilize a surface of a material. As a result, it is possible to effectively suppress adsorption of a protein or polypeptide to a material and to obtain a material with a high biocompatibility.

For a functional group capable of producing a silanol group through hydrolysis thereof, it is possible to provide a hydrosilyl group, an alkoxysilyl group, a halosilyl group, an acyloxysilyl group, an aminosilyl group, and the like, and an alkoxyl group with a carbon number of 1-6 or a hydrogen atom is preferable from the viewpoint of the stability, reactivity, or the like of a hydrolyzable polymer.

A material whose surface is to be modified is not particularly limited and it is possible to provide a resin material such as a PP (polypropylene), a polycarbonate, a PET (polyethyleneterephthalate), PEEK, a fluororesin, a polystyrene or vinyl chloride; a metallic material such as gold, titanium, aluminum, iron, copper or a stainless-steel; or a metal oxide such as alumina, titanium oxide or zinc oxide. Herein, as a surface modification method according to the present invention is used, it is possible to hydrophilize a material which is difficult to apply plasma treatment thereto, such as PEEK or a fluororesin.

Furthermore, a shape of a material whose surface is to be modified is not particularly limited and it is possible to provide a sheet shape, a particle shape, a tubular shape, or the like.

In the present invention, as an application fluid containing a hydrolyzable polymer and an alkoxysilane is applied onto a material, the hydrolyzable polymer and the alkoxysilane are hydrolyzed to produce a silanol group. Furthermore, a hydrolyzable polymer is cross-linked by means of dehydration and condensation of silanol groups with one another to form a cross-linked polymer layer in which a silanol group is introduced. Specifically, after an application fluid is applied onto a material, water, an acid or an alkali is applied thereto or heating thereof is conducted. Furthermore, after water, an acid or an alkali is applied onto a material, an application fluid may be applied thereto. Moreover, water, an acid, or an alkali may be mixed into an application fluid. In this case, it is preferable to prepare an application fluid at a time of application appropriately because hydrolysis may be caused in the application fluid. Additionally, when water, an acid, or an alkali is used, heating may be conducted, but normally, reaction sufficiently proceeds at room temperature. Furthermore, even if water, an acid, or an alkali is not used, reaction gradually proceeds due to atmospheric moisture.

An acid or alkali to be used for hydrolysis is not particularly limited as long as it is possible to attain hydrolysis, whereby it is possible to mix and use two or more kinds thereof and it may be used as an aqueous solution.

For an application fluid, it is possible to use a hydrolyzable polymer and alkoxysilane which are dissolved or dispersed in an organic solvent. For an organic solvent, it is possible to provide an aliphatic hydrocarbon, an aromatic hydrocarbon, a chlorinated hydrocarbon, an ether-type solvent, an alcohol-type solvent such as a monohydric-tetrahydric aliphatic alcohol with a carbon number 1-4, a cellosolve-type solvent such as ethyl cellosolve or butyl cellosolve, dioxane, methyl acetate, diformamide, or the like.

The concentration of a hydrolyzable polymer in an application fluid is not particularly limited, whereby 0.001-20% by weight is preferable and 0.1-5% by weight is more preferable. If the concentration is less than 0.001% by weight, no sufficient effect may be obtained by one time treatment and if it is more than 20% by weight, an application property or the like may be degraded.

Furthermore, the weight ratio of a hydrolyzable polymer to an alkoxysilane is not particularly limited, whereby 0.01%-20% is preferable and 0.2%-5% is more preferable. If the weight ratio is less than 0.01% by weight, the strength of a cross-linked polymer layer may be insufficient, and if it is more than 20%, the amount of a silanol group introduced in a cross-linked polymer layer may be insufficient.

A method for applying an application fluid is not particularly limited and it is possible to provide a dip coating method, a spray coating method, a spin cast method, or the like.

Then, similarly to as described above, an application fluid containing a hydrophilizing agent having a functional group capable of producing a silanol group through hydrolysis thereof is applied onto a material on which a cross-linked polymer layer is formed, whereby the hydrophilizing agent is hydrolyzed to produce a silanol group, or an application fluid containing a hydrophilizing agent having a silanol group is applied onto a material on which a cross-linked polymer layer is formed. Furthermore, a surface of a material is hydrophilized by means of dehydration and condensation of a silanol group priginating from a hydrophilizing agent and a silanol group introduced in a cross-linked polymer layer. Additionally, when a hydrophilizing agent is hydrolyzed and where the water, acid or alkali described above sufficiently remains on a cross-linked polymer layer, water, an acid or an alkali may not need to be newly applied.

For an application fluid, it is possible to use a hydrophilizing agent which is dissolved or dispersed in an organic solvent. For an organic solvent, it is possible to provide an aliphatic hydrocarbon, an aromatic hydrocarbon, a chlorinated hydrocarbon, an ether-type solvent, an alcohol-type solvent such as a monohydric-tetrahydric aliphatic alcohol with a carbon number 1-4, a cellosolve-type solvent such as ethyl cellosolve or butyl cellosolve, dioxane, methyl acetate, diformamide, or the like.

The concentration of a hydrophilizing agent in an application fluid is not particularly limited, whereby 0.1-30% by weight is preferable and 1-10% by weight is more preferable. If the concentration is less than 0.1% by weight, no sufficient effect may be obtained by one time treatment and if it is more than 30% by weight, an application property or the like may be degraded.

In the present invention, a hydrolyzable polymer is not particularly limited as long as it is a polymer having a functional group capable of producing a silanol group through hydrolysis thereof, and it is possible to use a homopolymer or copolymer (referred to as a "polymer (A)" below) obtainable by polymerizing a monomer (A-1) represented by the general formula:

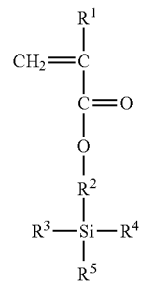

(In the formula, R1 is a hydrogen atom or a methyl group, R2 is an alkylene group with a carbon number of 1-6, and preferably a propylene group, and each of $R^3$, $R^4$, and R5 is independently an alkoxyl group with a carbon number of 1-6, and preferably, a methoxyl group or an ethoxyl group.). Herein, two or more kinds of monomers (A-1) may be used.

Furthermore, when a polymer (A) is synthesized, a monomer (A-2) may be copolymerized which is represented by the general formula:

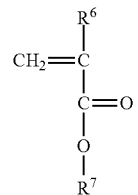

(In the formula, R6 is a hydrogen atom or a methyl group and R7 is a linear, branched or cyclic alkyl group with a carbon number of 1-18, preferably an alkyl group with a carbon number of 1-6, and more preferably a methyl group.). Herein, two or more kinds of monomers (A-2) may be used.

Moreover, when a polymer (A) is synthesized, a monomer (A-3) may be copolymerized which is represented by the general formula:

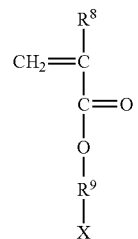

(In the formula, R8 is a hydrogen atom or a methyl group, R9 is an alkylene group with a carbon number of 1-6, preferably an ethylene group, a propylene group, or a 2-hydroxypropylene group, and X is:

a functional group (X-1) represented by the general formula:

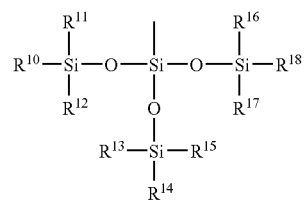

(In the formula, each of $R^{10}$, $R^{11}$, $R^{12}$, $R^{13}$, $R^{14}$, $R^{15}$, $R^{16}$, $R^{17}$, and $R^{18}$ is independently a linear or branched alkyl group with a carbon number of 1-6, and preferably a methyl group.), a functional group (X-2) represented by the general formula:

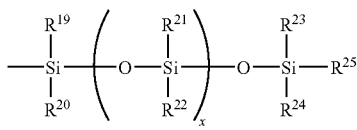

(In the formula, each of $R^{19}$, $R^{20}$, $R^{21}$, $R^{22}$, $R^{23}$, and $R^{24}$ is independently a linear or branched alkyl group with a carbon number of 1-6 and preferably a methyl group, $R^{25}$ is a linear or branched alkyl group with a carbon number of 1-6 and preferably a butyl group, and x is a positive integer.), or a functional group (X-3) represented by the general formula:

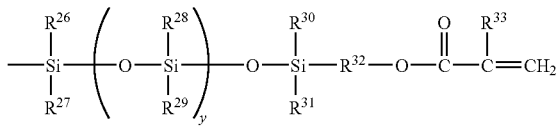

(In the formula, each of $R^{26}$, $R^{27}$, $R^{28}$, $R^{29}$, $R^{30}$, and $R^{31}$ is independently a linear or branched alkyl group with a carbon number of 1-6 and preferably a methyl group, $R^{32}$ is an alkylene group with a carbon number of 1-6 and preferably an ethylene group, a propylene group or a 2-hydroxypropylene group, $R^{33}$ is a hydrogen atom or a methyl group, and y is a positive integer.).). Additionally, when X is a functional group (X-2) or (X-3), the molecular weight of a monomer (A-3) is preferably 1,000-100,000 and more preferably 2,000-20,000. Herein, two or more kinds of monomers (A-3) may be used.

Furthermore, when a polymer (A) is synthesized, a monomer (A-4) may be copolymerized which is represented by the general formula:

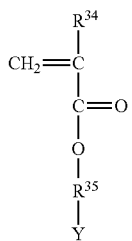

(In the formula, $R^{34}$ is a hydrogen atom or a methyl group, $R^{35}$ is an alkylene group with a carbon number of 1-6 and preferably an ethylene group or a propylene group, and Y is:

a functional group (Y-1) represented by the general formula:

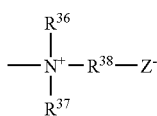

(In the formula, each of $R^{36}$, $R^{37}$, and $R^{38}$ is independently an alkyl group with a carbon number of 1-6 and preferably a methyl group, and $Z^-$ is a halide ion or a conjugate ion of an organic acid or inorganic acid.) or a functional group (Y-2) represented by the general formula:

(In the formula, each of $R^{39}$ and $R^{40}$ is independently an alkyl group with a carbon number of 1-6 and preferably a methyl group.).). Herein, two or more kinds of monomers (A-4) may be used.

That is, when a polymer (A) is synthesized, at least one of a monomer (A-2), monomer (A-3) and monomer (A-4) may be copolymerized with a monomer (A-1).

The content of a monomer (A-1) in the total amount of monomers used when a polymer (A) is synthesized is preferably 40-85% by weight. If this content is less than 40% by weight, a crosslink density may be lowered so that the effect of hydrophilization may not sufficiently proceed, and if it is more than 85% by weight, the uniformity of a cross-linked polymer layer may be degraded.

Furthermore, the content of a monomer (A-2) in the total amount of monomers used when a polymer (A) is synthesized is preferably 1% by weight or more and more preferably 10% by weight or more. If this content is less than 1% by weight, the water resistance of a cross-linked polymer layer may be degraded. Moreover, the content of a monomer (A-2) in the total amount of monomers used when a polymer (A) is synthesized is preferably 75% by weight or less and more preferably 60% by weight or less. If this content is more than 75% by weight or more, a polymer (A) may be insoluble in an alcohol-type solvent.

Furthermore, the content of a monomer (A-3) in the total amount of monomers used when a polymer (A) is synthesized is preferably 1% by weight or more and more preferably 5% by weight or more. If this content is less than 1% by weight, the water resistance of a cross-linked polymer layer may be degraded. Moreover, the content of a monomer (A-3) in the total amount of monomers used when a polymer (A) is synthesized is preferably 70% by weight or less and more preferably 60% by weight or less. If this content is more than 70% by weight or more, a polymer (A) may be insoluble in an alcohol-type solvent.

Furthermore, the ratio of the weight of a monomer (A-4) to the total weight of a monomer (A-1), monomer (A-2) and monomer (A-3) is preferably 0.01-1 and more preferably 0.05-0.5. If this ratio is less than 0.01, the flexibility of a cross-linked polymer layer may be degraded and if it is more than 1, the water resistance of a cross-linked polymer layer may be degraded.

The number-average molecular weight of a polymer (A) is not particularly limited as long as it has a polymerization degree equal to or more than that of an oligomer, and preferably 2,000-150,000. If the number-average molecular weight is less than 2,000, a period of time for forming a cross-linked polymer layer may be long, and if it is more than 150,000, the viscosity of an application fluid may be so high that an application property or workability thereof may be degraded.

Additionally, a specific example and manufacturing method of a polymer (A) are disclosed in Japanese Patent Application Publication No. 11-302129.

For a hydrolyzable polymer, it is also possible to use a homopolymer or copolymer (referred to as a "polymer (B)" below) having a structural unit (B-1) represented by the general formula:

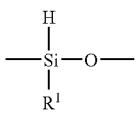

(In the formula, R1 is an alkyl group with a carbon number of 1-22 or a phenyl group, and preferably a methyl group.). Herein, a polymer (B) may have two or more kinds of structural units (B-1).

Furthermore, a polymer (B) may have a structural unit (B-2) represented by the general formula:

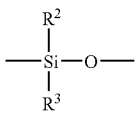

(In the formula, each of R2 and R3 is independently an alkyl group with a carbon number of 1-22 or a phenyl group and preferably a methyl group.). Herein, a polymer (B) may have two or more kinds of structural units (B-2).

The content of a structural unit (B-1) in a polymer (B) is preferably 1-90% by weight. If this content is less than 1% by weight, a crosslink density may be lowered so that the effect of hydrophilization may not sufficiently proceed, and if it is more than 90% by weight, the uniformity of a cross-linked polymer layer may be degraded.

Moreover, the content of a structural unit (B-2) in a polymer (B) is preferably 10-99% by weight. If this content is less than 10% by weight, the uniformity of a cross-linked polymer layer may be degraded, and if it is more than 99% by weight, a crosslink density may be lowered so that the effect of hydrophilization may not sufficiently proceed.

The number average molecular weight of a polymer (B) is not particularly limited as long as it has a polymerization degree equal to or more than that of an oligomer, and preferably 2,000-500,000. If the number average molecular weight is less than 2,000, a period of time for forming a cross-linked polymer layer may be long, and if it is more than 500,000, the viscosity of an application fluid may be so high that an application property or workability may be degraded.

In the present invention, for a hydrolyzable polymer, a polymer (A) and a polymer (B) may be used in combination and a hydrolyzable polymer and a non-hydrolyzable polymer may be used in combination. A non-hydrolyzable polymer is not particularly limited and it is possible to provide a polymer (A) or polymer (B) having no functional group capable of producing a silanol group through hydrolysis thereof or the like.

In the present invention, a hydrophilizing agent preferably has a functional group represented by the general formula:

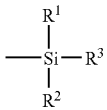

(In the formula, R1 is an alkoxyl group with a carbon number of 1-6 or a hydroxyl group, and preferably a methoxyl group, an ethoxyl group, or a hydroxyl group, and each of R2 and R3 is independently an alkoxyl group with a carbon number of 1-6, a hydroxyl group, or an alkyl group with a carbon number of 1-6, and preferably a methoxyl group, an ethoxyl group or a hydroxyl group.).

A hydrophilizing agent is not particularly limited as long as it is a compound having a functional group capable of producing a silanol group through hydrolysis thereof or a silanol group and a hydrophilic group, and it is possible to use a hydrophilizing agent (A) represented by the general formula:

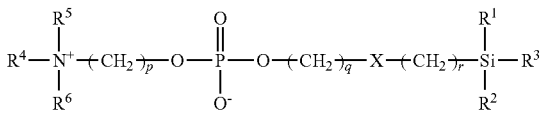

(In the formula, R1 is an alkoxyl group with a carbon number of 1-6 or a hydroxyl group and preferably a methoxyl group, each of R2 and R3 is independently an alkoxyl group with a carbon number of 1-6, a hydroxyl group or an alkyl group with a carbon number of 1-6 and preferably a methoxyl group, each of $R^4$, $R^5$, and R6 is independently an alkyl group with a carbon number of 1-6 and preferably a methyl group, X is a hetero-atom-containing bond such as an amide bond, an ester bond, an imino group, an oxy group, a urea bond, or a urethane bond, or a single bond and preferably an amide bond, and each of p, q, and r is independently an integer of 1-6.). Herein, two or more kinds of hydrophilizing agents (A) may be used in combination.

Additionally, a specific example and manufacturing method of a hydrophilizing agent (A) are disclosed in, for example, Japanese Patent Application Publication No. 2006-011380.

For a hydrophilizing agent, it is also possible to use a hydrophilizing agent (B) represented by the general formula:

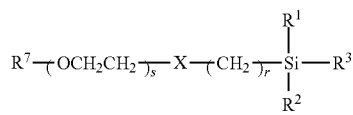

(In the formula, R1 is an alkoxyl group with a carbon number of 1-6 or a hydroxyl group and preferably an ethoxyl group, each of R2 and R3 is independently an alkoxyl group with a carbon number of 1-6, a hydroxyl group, or an alkyl group with a carbon number of 1-6, and preferably an ethoxyl group, X is a hetero-atom-containing bond such as an amide bond, an ester bond, an imino group, an oxy group, a urea bond or a urethane bond or a single bond and preferably an ester bond, R7 is a hydrogen atom or an alkyl group with a carbon number of 1-6 and preferably a hydrogen atom, r is an integer of 1-6, and s is an integer of 1-100.). Herein, two or more kinds of hydrophilizing agents (B) may be used in combination.

For a hydrophilizing agent, it is also possible to use a hydrophilizing agent (C) represented by the general formula:

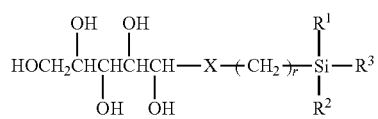

(In the formula, R1 is an alkoxyl group with a carbon number of 1-6 or a hydroxyl group and preferably an ethoxyl group, each of R2 and R3 is independently an alkoxyl group with a carbon number of 1-6, a hydroxyl group or an alkyl group with a carbon number of 1-6 and preferably an ethoxyl group, X is a hetero-atom-containing bond such as an amide bond, an ester bond, an imino group, an oxy group, a urea bond or urethane bond, or a single bond and preferably an amide bond, and r is an integer of 1-6.). Herein, two or more kinds of hydrophilizing agents (C) may be used in combination.

For a hydrophilizing agent, it is also possible to use a hydrophilizing agent (D) represented by the general formula:

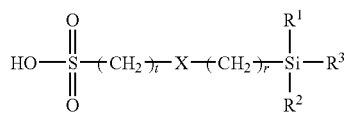

(In the formula, R1 is an alkoxyl group with a carbon number of 1-6 or a hydroxyl group and preferably a hydroxyl group, each of R2 and R3 is independently an alkoxyl group with a carbon number of 1-6, a hydroxyl group or an alkyl group with a carbon number of 1-6 and preferably a hydroxyl group, X is a hetero-atom-containing bond such as an amide bond, an ester bond, an imino group, an oxy group, a urea bond or urethane bond, or a single bond and preferably a single bond, each of r and t is independently an integer of 1-6, and where X is a single bond, r+t is an integer of 2-12.). Herein, two or more kinds of hydrophilizing agents (D) may be used in combination.

In the present invention, two or more kinds of a hydrophilizing agent (A), hydrophilizing agent (B), hydrophilizing agent (C), and hydrophilizing agent (D) may be used in combination for a hydrophilizing agent.

A surface of a material is modified by using a surface modification method according to the present invention whereby it is possible to obtain a material excellent in a biocompatibility and hydrophilicity thereof. It is possible to apply such a surface modified material to an application such as a cosmetic material, a medical material such as an artificial organ or a tool for operation, a filler for chromatography, an affinity particle, or a coating material.

PRACTICAL EXAMPLE 1

After 6.0 g of 3-methacryloyloxypropyltriethoxysilane (monomer A1), 3.5 g of methyl methacrylate (monomer A2), 0.5 g of 3-methacryloyloxypropyltris(trimethylsilyloxy)silane (monomer A-3), and 1.0 g of 2-methacryloyloxyethyltrimethylammonium chloride (monomer A4) were dissolved in 100 ml of ethanol and heating and stirring were conducted at 70° C. for 1 hour in a nitrogen stream, 0.05 g of potassium persulfate was added and copolymerization reaction was conducted overnight. Then, after reaction liquid was cooled to room temperature, vacuum concentration was conducted. After an obtained residue being dissolved in 10 ml of ethanol was added into 500 ml of n-hexane, a precipitate was fractionated to obtain polymer (A).

After a pp plate (1 cm×1 cm) washed with 2-propanol was dipped into a mixed liquid composed of 2 ml of 2-propanol, 1 g of tetraethylorthosilicate, 100 mg of polymer (A) and 100 μl of 1 M aqueous solution of sodium hydroxide, drying was conducted at 70° C. for 10 minutes.

After an application liquid in which 1 g of hydrophilizing agent (A) ($R^1$, $R^2$, and $R^3$: methoxyl groups, $R^4$, $R^5$, and $R^6$: methyl groups, X: amide bond, p=2, q=1, and r=2) was dissolved in 100 ml of methanol was applied onto an obtained polypropylene plate and drying was conducted at room temperature for 5 hours, rinsing and drying were conducted.

PRACTICAL EXAMPLE 2

A treatment similar to practical example 1 was conducted except that a PET plate (1 cm×1 cm) was used instead of the PP plate (1 cm×1 cm).

PRACTICAL EXAMPLE 3

A treatment similar to practical example 1 was conducted except that a polycarbonate plate (1 cm×1 cm) was used instead of the PP plate (1 cm×1 cm).

PRACTICAL EXAMPLE 4

A treatment similar to practical example 1 was conducted except that a gold-deposited glass plate (1 cm×1 cm) was used instead of the PP plate (1 cm×1 cm).

PRACTICAL EXAMPLE 5

A treatment similar to practical example 1 was conducted except that methylhydrogensilicone oil KF99 (produced by Shin-Etsu Chemical Co., Ltd.) was used instead of the polymer (A).

PRACTICAL EXAMPLE 6

A treatment similar to practical example 5 was conducted except that a titanium plate (1 cm×1 cm) was used instead of the PP plate (1 cm×1 cm).

PRACTICAL EXAMPLE 7

A treatment similar to practical example 1 was conducted except that N-(TRIETHOXYSILYLPROPYL)-O-POLYETHYLENE OXIDE URETHANE (produced by Gelest Inc.) that was a hydrophilizing agent (B) ($R^1$, $R^2$, and $R^3$: ethoxyl groups, $R^7$: a hydrogen atom, X: a urethane bond, r=3, and s=4-6) was used instead of the hydrophilizing agent (A).

PRACTICAL EXAMPLE 8

A treatment similar to practical example 1 was conducted except that N-(3-TRIETHOXYSILYLPROPYL)GLOCONAMIDE (produced by Gelest Inc.) that was a hydrophilizing agent (C) ($R^1$, $R^2$, and $R^3$: ethoxyl groups, X: an amide bond, and r=3) was used instead of the hydrophilizing agent (A).

PRACTICAL EXAMPLE 9

A treatment similar to practical example 1 was conducted except that a hydrophilizing agent (D) ($R^1$, $R^2$, and $R^3$: hydroxyl groups, X: a single bond, and r t=3) was used instead of the hydrophilizing agent (A).

[Contact Angle Measurement]

Contact angles for the plates before and after treatments of practical examples 1-9 were measured by using an automatic contact angle meter Type CA-V150 (produced by FACE Inc.). The results of measurements are illustrated in Table 1.

TABLE 1

| | Pre-treatment [°] | Post-treatment [°] |
|---|---|---|
| Practical example 1 | 92 | 4 |
| Practical example 2 | 74 | 10 |
| Practical example 3 | 99 | 8 |
| Practical example 4 | 98 | 7 |
| Practical example 5 | 92 | 15 |
| Practical example 6 | 78 | 10 |
| Practical example 7 | 92 | 11 |
| Practical example 8 | 92 | 13 |
| Practical example 9 | 92 | 4 |

From Table 1, it is found that the surfaces of the plates after treatments of practical examples 1-9 were modified and hydrophilized.

[Protein Adsorption Test]

A protein adsorption test was conducted by using a 24-well plate made of polystyrene and subjected to treatment similar to that of practical example 1. Specifically, 100 μl/well of a 1 mg/ml phosphate-buffered solution of a protein (albumin (Alb), IgG or lysozyme (Lyz)) was first added to the well plate before and after the treatment and incubated at 37° C. for 1 hour. Then, washing with a phosphate-buffered solution was conducted 5 times. Furthermore, absorbance (wavelength: 562 nm) of the well plate before and after the treatment was measured by using a micro BCA kit, whereby the quantity of the protein adsorbed on the well plate before and after the treatment were estimated. The results of the estimation are illustrated in FIG. 1. Additionally, the longitudinal axis of FIG. 1 indicates the ratio of the absorbance of the well plate after the treatment to that of the well plate before the treatment. From FIG. 1, it is found that the absorbance of the well plate was reduced by the treatment with respect to any protein of albumin, IgG and lysozyme. Accordingly, it is found that the well plate after the treatment suppressed adsorption of the protein.

[Appendix]

While taking a problem possessed by the aforementioned conventional techniques into consideration, at least one embodiment of the present invention is intended to provide a surface modification method capable of introducing a phosphorylcholine-like group in a surface of a material such as a PEEK or a fluororesin and a surface modification material whose surface is modified by using the surface modification method.

Embodiment (1) of the present invention is a surface modification method characterized by including a step of applying, onto a material, an application fluid containing a polymer having a functional group capable of producing a silanol group through hydrolysis thereof and an alkoxysilane and a step of applying, onto the material on which the application fluid is applied, an application fluid containing a hydrophilizing agent having a functional group capable of producing a silanol group through hydrolysis thereof or a silanol group.

Embodiment (2) of the present invention is a surface modification method according to embodiment (1) of the present invention, characterized in that the polymer is a homopolymer or copolymer obtainable by polymerizing a monomer represented by the general formula:

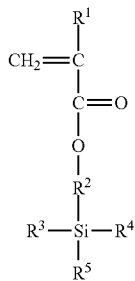

(In the formula, $R^1$ is a hydrogen atom or a methyl group, $R^2$ is an alkylene group with a carbon number of 1 or more and 6 or less, and each of $R^3$, $R^4$, and $R^5$ is independently a functional group capable of producing a hydroxyl group through hydrolysis thereof.).

Embodiment (3) of the present invention is a surface modification method according to embodiment (2) of the present invention, characterized in that each of $R^3$, $R^4$, and $R^5$ is independently an alkoxyl group with a carbon number of 1 or more and 6 or less.

Embodiment (4) of the present invention is a surface modification method according to embodiment (1) of the present invention, characterized in that the polymer is a homopolymer or copolymer having a structural unit represented by the general formula:

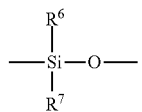

(In the formula, $R^6$ is a functional group capable of producing a hydroxyl group through hydrolysis thereof and $R^7$ is an alkyl group with a carbon number of 1 or more and 22 or less or a phenyl group.).

Embodiment (5) of the present invention is a surface modification method according to embodiment (4) of the present invention, characterized in that $R^6$ is a hydrogen atom.

Embodiment (6) of the present invention is a surface modification method according to any one of embodiments (1) to (5) of the present invention, characterized in that the hydrophilizing agent has a functional group represented by the general formula:

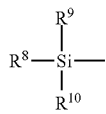

(In the formula, $R^8$ is a functional group capable of producing a hydroxyl group through hydrolysis thereof or a hydroxyl group, and each of $R^9$ and $R^{10}$ is independently a functional group capable of producing a hydroxyl group through hydrolysis thereof, a hydroxyl group, or an alkyl group with a carbon number of 1 or more and 6 or less.).

Embodiment (7) of the present invention is a surface modification method according to embodiment (6) of the present invention, characterized in that $R^8$ is an alkoxyl group with a carbon number of 1 or more and 6 or less and a hydroxyl group and each of $R^9$ and $R^{10}$ is independently an alkoxyl group with a carbon number of 1 or more and 6 or less, a hydroxyl group, or an alkyl group with a carbon number of 1 or more and 6 or less.

Embodiment (8) of the present invention is a surface modification method according to any one of embodiments (1) to (7) of the present invention, characterized in that the hydrophilizing agent has:

a functional group represented by the general formula:

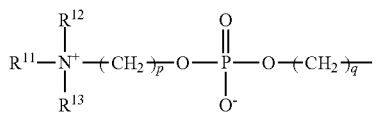

(In the formula, each of $R^{11}$, $R^{12}$ and $R^{13}$ is independently an alkyl group with a carbon number of 1 or more and 6 or less and each of p and q is independently an integer of 1 or more and 6 or less.), a functional group represented by the general formula:

(In the formula, $R^{14}$ is a hydrogen atom or an alkyl group with a carbon number of 1 or more and 6 or less and s is an integer of 1 or more and 100 or less.), a functional group represented by the chemical formula:

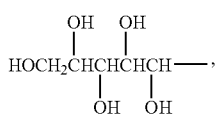

or a functional group represented by the general formula:

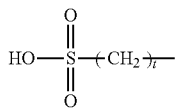

(In the formula, t is an integer of 1 or more and 6 or less.).

Embodiment (9) of the present invention is a surface modification material characterized in that a surface thereof is modified by using a surface modification method according to any one of embodiments (1) to (8) of the present invention.

According to at least one embodiment of the present invention, it is possible to provide a surface modification method capable of introducing a phosphorylcholine-like group in a surface of a material such as a PEEK or a fluororesin and a surface modification material whose surface is modified by using the surface modification method.

The present international application claims the priority based on Japanese Patent Application No. 2007-277361 filed on Oct. 25, 2007, and the entire content of Japanese Patent Application No. 2007-277361 is incorporated by reference in the present international application.

The invention claimed is:

1. A surface modification method, comprising the steps of:
applying a first application fluid containing a polymer having a functional group capable of producing a silanol group through hydrolysis thereof and an alkoxysilane onto a material; and
applying a second application fluid containing a hydrophilizing agent having a functional group capable of producing a silanol group through hydrolysis thereof or a silanol group onto the material with the applied first application fluid,
wherein the polymer is a homopolymer or copolymer having a structural unit represented by the general formula:

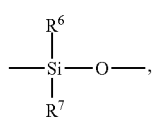

wherein $R^6$ is a functional group capable of producing a hydroxyl group through hydrolysis thereof and $R^7$ is an alkyl group with a carbon number of 1 or more and 22 or less or a phenyl group.

2. The surface modification method as claimed in claim 1, wherein $R^6$ is a hydrogen atom.

3. A surface modification method, comprising the steps of:
applying a first application fluid containing a polymer having a functional group capable of producing a silanol group through hydrolysis thereof and an alkoxysilane onto a material; and
applying a second application fluid containing a hydrophilizing agent having a functional group capable of producing a silanol group through hydrolysis thereof or a silanol group onto the material with the applied first application fluid,
wherein the hydrophilizing agent has:
a functional group represented by the chemical formula:

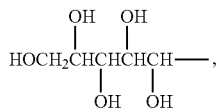

or a functional group represented by the general formula:

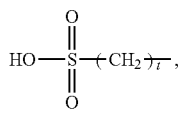

wherein t is an integer of 1 or more and 6 or less.

4. A surface modified material, comprising a surface modified by the surface modification method as claimed in claim 1.

5. A surface modified material, comprising a surface modified by the surface modification method as claimed in claim 3.

* * * * *